United States Patent
Docherty et al.

(10) Patent No.: US 7,914,759 B2
(45) Date of Patent: Mar. 29, 2011

(54) PRODUCTION OF BISPHOSPHINES

(75) Inventors: Gordon Docherty, Birmingham (GB); Graham Good, Oldbury (GB); Sheena Jackson, Birmingham (GB)

(73) Assignee: Rhodia UK Limited, Watfordhertfordshire (GB)

( * ) Notice: Subject to any disclaimer, the term of this patent is extended or adjusted under 35 U.S.C. 154(b) by 0 days.

(21) Appl. No.: 11/989,113

(22) PCT Filed: Jul. 20, 2006

(86) PCT No.: PCT/EP2006/064441
§ 371 (c)(1),
(2), (4) Date: May 12, 2009

(87) PCT Pub. No.: WO2007/010016
PCT Pub. Date: Jan. 25, 2007

(65) Prior Publication Data
US 2010/0015024 A1    Jan. 21, 2010

(30) Foreign Application Priority Data
Jul. 22, 2005  (GB) .................................. 0515082.6

(51) Int. Cl.
*C01B 25/00*    (2006.01)
(52) U.S. Cl. ....................................................... 423/299
(58) Field of Classification Search .................. None
See application file for complete search history.

(56) References Cited

U.S. PATENT DOCUMENTS
7,135,582 B2 *  11/2006  Goto et al. ....................... 556/21

FOREIGN PATENT DOCUMENTS
EP           1 452 537 A1      9/2004
WO     WO 2005/023823    *   3/2005

OTHER PUBLICATIONS

Porchia et al., {New Approach to the Chemistry of Technetium(V) and Rhenium(V) Phenylimido Complexes: Novel [M(NPh)PNP]3+ Metal Fragments (M=Tc, Re; PNP=Aminodiphosphine) Suitable for the Synthesis of Stable Mixed-Ligand Compounds, Inorganic Chemistry (2005), 44(13), 4766-4776}.*
Dani et al., {Complexes of Bis-ortho-cyclometalated Bisphosphinoaryl Ruthenium(II) Cations with Neutral Meta-bisphosphinoarene Ligands Containing an Agostic C-HoooRu Interaction, Organometallics (2000), 19(25), 5287-5296}.*
Miura et al., "Synthesis and Reactions of Optically Active Secondary Dialkylphosphine-Boranes", Journal of Organic Chemistry, Mar. 2, 2000, pp. 1877-1880, vol. 65, No. 6, American Chemical Society.

* cited by examiner

*Primary Examiner* — Yong Chu
*Assistant Examiner* — Chukwuma O Nwaonicha
(74) *Attorney, Agent, or Firm* — Buchanan Ingersoll & Rooney, PC.

(57) ABSTRACT

Bisphosphines are prepared by reacting a phosphine with a dihalide in the presence of an acid; characteristically, bisphosphonium compounds are initially formed and then converted into the bisphosphines.

20 Claims, No Drawings

PRODUCTION OF BISPHOSPHINES

CROSS-REFERENCE TO PRIORITY/PCT APPLICATIONS

This application claims priority under 35 U.S.C. §119 of GB 0515082.6, filed Jul. 22, 2005, and is a continuation of PCT/EP 2006/064441, filed Jul. 20, 2006 and designating the U.S. (published in the French language on Jan. 25, 2007, as WO 2007/010016 A2; the title and abstract were also published in English), each hereby expressly incorporated by reference in its entirety and each assigned to the assignee hereof.

The present invention relates to the production of bisphosphines.

Bisphosphines can be produced from the reaction of a phosphine with a dihalide. However, this reaction results in a linear bisphosphonium product and also a byproduct comprising a closed cyclic monophosphonium ring. This means that the yield of linear bisphosphonium product, and of bisphosphine which can be obtained therefrom, may be relatively low.

There does exist a need for a means for increasing the formation of the desired bisphosphonium product with respect to the monophosphonium byproduct and to thus improve the bisphosphine yield.

The present invention provides, in a first aspect, a process for the production of a bisphosphine, comprising the reaction of a phosphine with a dihalide in the presence of an acid.

Surprisingly, the incorporation of an acid in the reaction of a phosphine with a dihalide increases the formation of the desired bisphosphonium product and thus makes it possible to obtain an improved yield of the bisphosphine.

The acid, the phosphine and the dihalide can be combined in any order. For example, the acid can be added to a reactor comprising the phosphine and the dihalide, or the acid can be added to a reactor simultaneously with the phosphine and the dihalide, or the acid, the phosphine and the dihalide can be added to a reactor sequentially in any order.

The acid can be used in any suitable amounts, for example, according to a molar ratio with the dihalide (acid:dihalide) ranging from 0.005:1 to 5:1, such as from 0.01:1 to 3:1. In one embodiment, the acid is used in amounts of catalytic type. For example, the acid can be used according to a molar ratio with the dihalide (acid:dihalide) ranging from 0.01:1 to 0.1:1, such as from 0.03:1 to 0.08:1. In another embodiment, the acid is used in amounts of stoichiometric type. For example, the acid can be used according to a molar ratio with the dihalide (acid:dihalide) ranging from 0.5:1 to 2:1, such as from 0.75:1 to 1.25:1.

The acid can be any suitable acid, but it is preferably a strong acid. The acid suitably may have a pKa in water at 25° C. of 4.0 or less, for example a pKa of 3.0 or less, such as a pKa of 2.0 or less; preferably a pKa of 1.5 or less, for example a pKa of 1.0 or less, such as a pKa of 0.5 or less; more preferably a pKa of 0 or less, for example a pKa of −1.0 or less, such as a pKa of −1.5 or less; very preferably a pKa of −2.0 or less, for example a pKa of −2.5 or less, such as a pKa of −3.0 or less.

The acid is preferably an organic acid but, in an alternative embodiment, it can be an inorganic acid.

In one embodiment, the acid is a sulfur-comprising acid. For example, the acids can be sulfuric acid or a sulfonic acid. Examples of such acids are: fluorosulfonic acids (including fluoromethanesulfonic acid, difluoromethanesulfonic acid, trifluoromethane-sulfonic acid (triflic acid), trifluoroethanesulfonic acid, perfluorooctanesulfonic acid and perfluoro-4-methyl-3,6-dioxaoctanesulfonic acid); methanesulfonic acid; benzenesulfonic acid; sulfuric acid; oleum; and p-toluenesulfonic acid. The preferred acids are sulfur-comprising organic acids, in particular triflic acid and methanesulfonic acid.

Other examples of strong acids which can be used are nitric acid, hydrochloric acid and perchloric acid.

The dihalide is selected such as to correspond to the bisphosphine which it is desired to produce by the process. For example, if the required bisphosphine is an aromatic compound having two phosphine substituent groups, then the dihalide will be the analogous aromatic compound having two halogen substituent groups.

In one embodiment, the dihalide is a bis(halomethyl)benzene. In this case, the bisphosphine suitably may be a bis(alkylphosphinomethyl)benzene, for example a bis(di(tert-butyl)phosphinomethyl)benzene. The dihalide can be a 1,2-(ortho) or 1,3- (meta) or 1,4- (para) bis(halomethyl)benzene (corresponding to the desired bisphosphine respectively having a 1,2-(ortho) or 1,3-(meta) or 1,4- (para) substitution of the two phosphine-based groups on the benzene). In a preferred embodiment, the substitution is 1,2 substitution.

The halogen groups in the dihalide can be halogen groups of any type but they are preferably selected from chlorine, bromine and iodine groups. In a preferred embodiment, the dihalide is a dibromide.

Consequently, in one embodiment, the dihalide is 1,2-bis (bromomethyl)benzene.

The phosphine is selected so as to correspond to the phosphine substituents on the bisphosphine which it is desired to produce by this process. For example, if the required bisphosphine has secondary phosphine substituent groups ($R_2P$—, where each R, which can be identical or different, is a functional group), then the phosphine will be the analogous secondary phosphine $R_2PH$. Each R group can be appropriately selected from alkoxy, nitro, alkynyl and sulfonic acid groups and substituted or unsubstituted alkyl, aryl, amino and vinyl groups. It is preferable for each R group to comprise up to 20 carbon atoms, for example up to 12 carbon atoms, such as 0, 1, 2, 3 or 4 carbon atoms.

In one embodiment, the phosphine used is an alkylphosphine. In this case, the desired bisphosphine may suitably be a bis(alkylphosphinomethyl)benzene. Preferably, the phosphine is a dialkylphosphine ($R_2PH$, where each R is alkyl); in this case the desired bisphosphine can be a bis(dialkylphosphinomethyl)benzene. The alkyl may suitably be a $C_{1-8}$ alkyl such as methyl, ethyl, propyl, n-butyl or tert-butyl. For example, the phosphine can be a di(tert-butyl)phosphine; in this case the desired bisphosphine can be a bis(di(tert-butyl) phosphinomethyl)benzene.

The phosphine can be present in any suitable amount of stoichiometric type with respect to the dihalide, given that the production of a bisphosphine is envisaged. Consequently, the phosphine can be used according to a molar ratio with the dihalide (phosphine:dihalide) ranging from 2:1 to 5:1, such as from 2.5:1 to 4:1, for example from 3:1 to 3.5:1.

In one embodiment, the bisphosphine being produced is a 1,4-bisphosphine (the phosphor atoms are separated by 4 carbons).

The reaction may be carried out under all suitable conditions and for any suitable period of time. Use may be made of the reaction times and conditions as known in the art for the production of conventional bisphosphine by reaction of a phosphine with a dihalide.

For example, the reaction can be carried out in any suitable solvent, for example an organic solvent, such as acetone. The reaction can be carried out at any suitable temperature, for example, at the reflux temperature or close to the latter.

The process suitably comprises a stage of conversion to the corresponding bisphosphine of the bisphosphonium product which has been obtained from the reaction of phosphine and dihalide in the presence of an acid.

In one embodiment, the process comprises the stage of reaction: (I) of the bisphosphonium product obtained from the reaction of the phosphine with the dihalide in the presence of an acid; and (II) of a base.

Consequently, the invention provides a process for the production of bisphosphine, which process comprises:
a) the reaction of phosphine with a dihalide in the presence of an acid to result in a bisphosphonium product; and
b) the reaction of the bisphosphonium product obtained from stage (a) with a base.

Optionally, the bisphosphonium product obtained from stage (a) can be isolated before carrying out stage (b).

The preferred characteristics for stage (a) are as defined above.

The base used in stage (b) can be any suitable base. Preferably the base is a weak base. The base can suitably have a pKb in water at 25° C. of 0 or more; for example a pKb of 1.0 or more; preferably a pKb of 2.0 or more, for example a pKb of 3.0 or more, such as a pKb of 4.0 or more; more preferably a pKb of 5.0 or more, for example a pKb of 6.0 or more, such as a pKb of 7.0 or more. Examples of suitable bases comprise sodium acetate trihydrate, potassium acetate trihydrate, sodium carbonate or potassium carbonate. The base is conveniently used in the form of a solution, for example an aqueous solution.

The present invention also provides, in a second aspect, the use of an acid for increasing the yield of bisphosphonium or bisphosphine products in a reaction.

The acid can be as described above in the context of the first aspect.

Preferably, the use occurs in a process for the production of bisphosphine comprising the reaction of a phosphine with a dihalide.

In the preferred embodiments, the reaction is as defined above in the context of the first aspect.

In a third aspect of the invention, a process for the production of a metal complex is provided, which comprises:
(i) the production of a bisphosphine by carrying out a process in accordance with the first aspect of the invention; and
(ii) the reaction of one or more molecules of the bisphosphine obtained from stage (i) with a source of metal salt.

Optionally, the bisphosphine obtained from stage (i) can be isolated before carrying out stage (ii).

The preferred characteristics for stage (i) are as defined above in the context of the first aspect.

The metal salt can be any metal salt but is preferably a salt providing a transition metal ion or atom, more preferably an ion or atom of a transition metal from Group 8, 9 or 10, very preferably a ruthenium, iridium, rhodium or palladium ion or metal, for example, ruthenium(II).

The present invention will now be further illustrated by means of the following examples:

COMPARATIVE EXAMPLE 1

A mixture of di(tert-butyl)phosphine (9 g, 61.6 mmol) and dibromo-o-xylene (5 g, 18.9 mmol) was heated at reflux in the presence of acetone (20 ml). The resulting solution was left to mature for one hour and then cooled down to <10° C.

An off-white solid (6.7 g) was subsequently isolated from the cold product by filtration. A portion of this solid (3 g, 5.4 mmol) was subsequently treated with a dilute base (4.6 g, 33.8 mmol, sodium acetate trihydrate in 14 ml of degassed water). The precipitated solid was subsequently taken up in ether (14 ml) and isolated by removal of the aqueous component and subsequent evaporation of the ether. An off-white solid crystallized during the cooling.

The yield of 1,2-bis(di(tert-butyl)phosphinomethyl)benzene was 33%.

EXAMPLE 1

A mixture of di(tert-butyl)phosphine (9 g, 61.6 mmol), triflic acid (0.23 g, 1.5 mmol) and dibromo-o-xylene (5 g, 18.9 mmol) was heated at reflux in the presence of acetone (20 ml). The resulting solution was left to mature for 1 hour and then cooled down to <10° C.

An off-white solid (6.6 g) was subsequently isolated from the cold product by filtration. A portion of this solid (3 g, 5.4 mmol) was treated with a dilute base (4.6 g, 33.8 mmol, sodium acetate trihydrate in 14 ml of degassed water). The precipitated solid was subsequently taken up in ether (14 ml) and isolated by removal of the aqueous component and subsequent evaporation of the ether. An off-white solid crystallized during the cooling.

The yield of 1,2-bis(di(tert-butyl)phosphinomethyl)benzene was 41%.

Consequently, it may be observed that, from the example in accordance with the invention, a bisphosphine yield was obtained which is significantly improved in comparison with that of the comparative example.

What is claimed is:

1. A process for the preparation of a bisphosphine, comprising reacting a secondary phosphine of the formula $R_2PH$, in which each R, which can be identical or different, is selected from the group consisting of alkoxy, nitro, alkynyl, sulfonic, alkyl, aryl, amino and vinyl groups, wherein the alkyl, aryl, amino and vinyl groups are unsubstituted or substituted, and each R group comprises up to 20 carbon atoms, with a bis(halomethyl)benzene in the presence of an organic sulfonic acid whose pKa is −2.0 or less.

2. The process as defined by claim 1, wherein the molar ratio of the organic sulfonic acid to the bis(halomethyl)benzene ranges from 0.01:1 to 0.1:1.

3. The process as defined by claim 2, wherein the molar ratio of the organic sulfonic acid to the bis(halomethyl)benzene ranges from 0.03:1 to 0.08:1.

4. The process as defined by claim 1, in which the bis(halomethyl)benzene is a 1,2-bis(halomethyl)benzene.

5. The process as defined by claim 1, in which the bis(halomethyl)benzene is bis(bromomethyl)benzene.

6. The process as defined by claim 1, in which R is a $C_{1-8}$ alkyl radical.

7. The process as defined by claim 1, in which the secondary phosphine is di(tert-butyl)phosphine.

8. The process as defined by claim 1, wherein said process comprises: forming a biphosphonium compound by reacting a phosphine with a dihalide in the presence of an acid to form a bisphosphonium compound and thence converting the bisphosphonium compound into a corresponding bisphosphine.

9. The process as defined by claim 8, wherein the step of converting the bisphosphonium compound into the corresponding biphosphine comprises reacting the bisphosphonium compound with a base.

10. The process as defined by claim 9, in which the bisphosphonium product is isolated before being reacted with the base.

11. The process as defined by claim 9, in which the base is a weak base.

12. The process as defined by claim 9, in which the base has a pKb of 2.0 or more.

13. A process for the production of a metal complex, comprising the steps of:
(i) preparing a bisphosphine by reacting a secondary phosphine of the formula $R_2PH$, in which each R, which can be identical or different, is selected from the group consisting of alkoxy, nitro, alkynyl, sulfonic, alkyl, aryl, amino and vinyl groups, wherein the alkyl, aryl, amino and vinyl groups are unsubstituted or substituted, and each R group comprises up to 20 carbon atoms, with a bis(halomethyl)benzene in the presence of an organic sulfonic acid whose pKa is −2.0 or less.;
(ii) reacting the bisphosphine with a metal salt.

14. The process as defined by claim 13, in which the bisphosphine prepared in step (i) is isolated before carrying out step (ii).

15. The process as defined by claim 13, in which the metal salt is a salt providing a transition metal ion or atom.

16. The process of claim 1, wherein the organic sulfonic acid is selected from the group consisting of fluoromethanesulfonic acid, difluoromethanesulfonic acid, trifluoromethane-sulfonic acid (triflic acid), trifluoroethanesulfonic acid, perfluorooctanesulfonic acid, perfluoro-4-methyl-3,6-dioxaoctanesulfonic acid, methanesulfonic acid, benzenesulfonic acid, and p-toluenesulfonic acid.

17. The process of claim 16, wherein each functional group R comprises up to 12 carbon atoms.

18. The process of claim 16, wherein each functional group R comprises 0, 1, 2, 3 or 4 carbon atoms.

19. The process of claim 13, wherein the metal salt comprises a transition metal from Group 8, 9 or 10 of the Periodic Table.

20. The process of claim 13, wherein the metal salt comprises a ruthenium, iridium, rhodium or palladium ion or metal.

\* \* \* \* \*